United States Patent [19]

Newton

[11] 4,082,994
[45] Apr. 4, 1978

[54] VAPOR/LIQUID FRACTION DETERMINATION

[75] Inventor: Robert E. Newton, Tewksbury, Mass.

[73] Assignee: Auburn International, Inc., Danvers, Mass.

[21] Appl. No.: 722,168

[22] Filed: Sep. 10, 1976

Related U.S. Application Data

[63] Continuation-in-part of Ser. No. 719,196, Aug. 31, 1976.

[51] Int. Cl.² ............................................. G01N 27/42
[52] U.S. Cl. .............................. 324/30 R; 204/195 R
[58] Field of Search ..................... 324/29, 65 R, 30 R, 324/30 A, 30 B; 204/1 T, 195 R

[56] References Cited

U.S. PATENT DOCUMENTS

| | | | |
|---|---|---|---|
| 2,004,569 | 6/1935 | Davis, Jr. | 324/30 R |
| 2,760,922 | 8/1956 | Williams, Jr. | 324/30 R |
| 3,040,245 | 6/1962 | Brizzolara | 324/30 R |
| 3,368,144 | 2/1968 | Gerdes | 324/30 R |

*Primary Examiner*—M. Tokar
*Attorney, Agent, or Firm*—Jerry Cohen

[57] ABSTRACT

The relative amounts of liquid phase versus vapor phase of a mixed phase resistively conductive fluid, such as boiling water, is determined by an indirect measurement of admittance between a poled pair of electrodes within a cross section of a flow path in the fluid comprising part of an electrical circuit by providing an oscillating power source therein with an alternating voltage on the order of 1–30 kilohertz across the electrode pair generating a voltage drop across a load resistance in the loop which electric parameter varies as a function of admittance in the fluid between electrodes—as affected by liquid void fractions therein, the voltage drop signal so produced being divided by a similar voltage drop which varies as a function of admittance of liquid from the same fluid to determine liquid fraction (and by subtraction from unity, vapor fraction), with compensation for conductivity change, the measuring process further including the isolation of reactive and resistive cross conduction outside the measurement loop.

9 Claims, 5 Drawing Figures

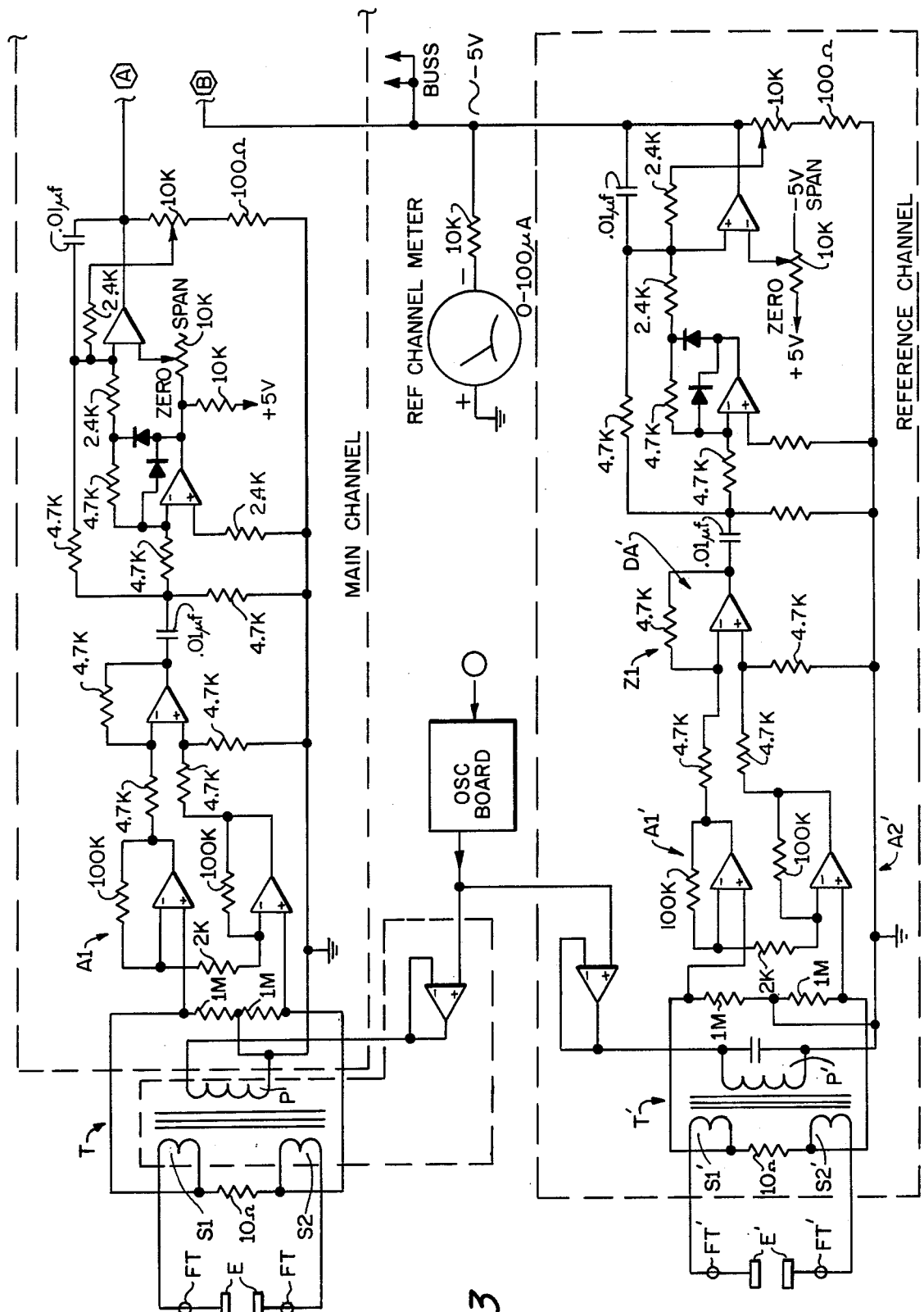
FIG. 3 PART 1

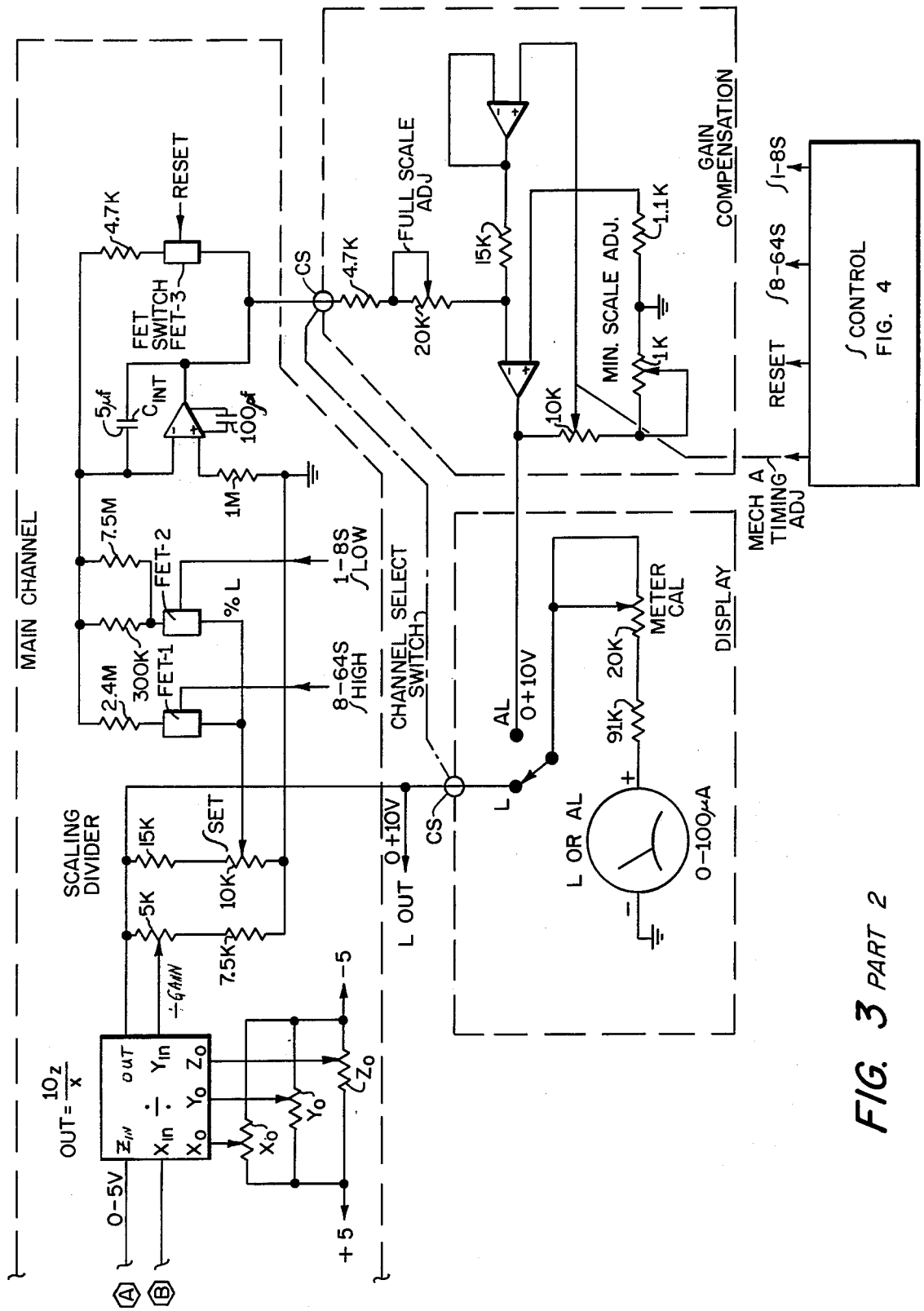
FIG. 3 PART 2

VAPOR/LIQUID FRACTION DETERMINATION

CROSS REFERENCE TO RELATED APPLICATIONS

This application is a continuation-in-part of U.S. patent application Ser. No. 719,196 filed Aug. 31, 1976, by Newton, Grimaldi and Dechene, of common assignment with this application, the disclosure of which is incorporated herein by reference as though set out at length herein.

BACKGROUND OF THE INVENTION

The present invention relates to measuring relative fractions of liquid and vapor in mixed phase conductive fluids, such as occurs in boiling water, non-boiling turbulent flows, fluidized bed experiments, water-gas mixing analysis, nuclear plant cooling and other diverse applications.

The prior art includes a number of mechanical and electrical approaches to the problems. There have also been a number of attempts to measure the voidage or fractional vapor content in conductive fluids such as water by measuring the total capacitance of a section of the fluid, making use of the Clausius-Mosotti relationship to determine the fractional vapor content. Such an approach has the advantage of being easily calibrated since with reasonably simple sensor geometries, there is a linear relationship between average dielectric constant and liquid fraction. This technique works well in liquids of essentially zero conductivity but gives very poor or even completely erroneous results in liquids of even very low conductivity such as water.

The reason for this is that with currently attainable operating frequencies, the levels of capacitive currents are usually several orders of magnitude smaller than the resistive components. Even if the measuring system front end amplifiers can be kept from saturating on the large resistive current, in itself no small task, the presence of extremely small and unavoidable phase shifts in the signal circuits (fractions of a degree) will shift enough of the resistive component of current into the apparent capacitive domain to completely overwhelm the actual capacitive currents.

Another serious problem arises in the contact interface between the sensor and the liquid. Electrical contact is necessary, since otherwise the electric field will be developed across the insulator and not the fluid. Any measurements obtained with insulated sensors give more information about the quality of the insulation than about the fluid in the sensor region.

In view of these problems with capacitive measurements, recent work has been done in measuring the resistive component of the sensor current. This has the substantial advantage that sensor current is fairly large and easy to measure. However, there are three main difficulties associated with this approach. First, the calibration technique for determining voidage is more complex than in the capacitive case. It is not usually possible to arrive at a predicted relationship between measured conductivity and voidage. Instead, measurements must usually be made with various known levels of voidage and an empirical relationship derived.

Second, it is not possible to measure void content near 100%. If the resistive path across the sensor is broken, no measurements can be made. In many cases, this limitation is not a serious one.

Finally, conductive fluids such as water tend to undergo fairly dramatic changes in conductivity as a result of often uncontrollable circumstances such as absorption of carbon dioxide or other gases from the air and the possible leaching out of ionic salts from the containers and tubing. This problem can usually be overcome by making all measurements with respect to a reference sensor immersed with a sample of the test fluid. This sample must be representative of the fluid in the sensor and must contain no voidage.

It is an important object of the invention to provide vapor and liquid fraction measurement in a mixed flow affectively substantially free of the above problems.

It is a further object of the invention to provide a simple construction making a minimal disturbance on the system being measured consistent with the preceding objects.

It is a further object of the invention to screen out sources of spurious reading consistent with one or more of the preceding objects.

It is a further object of the invention to provide an economical device consistent with one or more of the preceding objects.

SUMMARY OF THE INVENTION

In accordance with the invention, an electrical parameter measurement is made in a closed resistive conductivity loop including an electrolytic path through the cross section of the fluid to be measured. Such parameter, preferrably voltage drop across a load resistance in the loop is affected by admittance in the electrolytic path portion of the loop. The driving voltage for producing a measuring current is preferably high frequency voltage oscillation. A separate measurement of 100% liquid derived from the electrolytic fluid may be made in the same fashion and divided into the main loop parameter measurement to compensate for bulk conductivity changes in the fluid being measured. The frequency of the field applied for conductivity measurement is preferably from 1–30 kilohertz, more preferably 5 kilohertz, i.e., greater than common power frequencies and much lower than radio frequencies. Readings of conductivity are taken through high impedance connection to the flow loop and the voltage excitation of the loop is preferably through an isolation transformer of low output impedance such that changes in conductivity in the flow medium primarily control current through a loop. Measurements may be taken at a single electrode pair station or multiple electrode pair stations, in either case on a real time or averaged basis. Measurements may be stored for later reading.

Other objects, features and advantages of the invention will be apparent from the following detailed description of preferred embodiments thereof taken in connection with the accompanying drawing, in which,

DETAILED DESCRIPTION OF PREFERRED EMBODIMENTS

Figure 1:
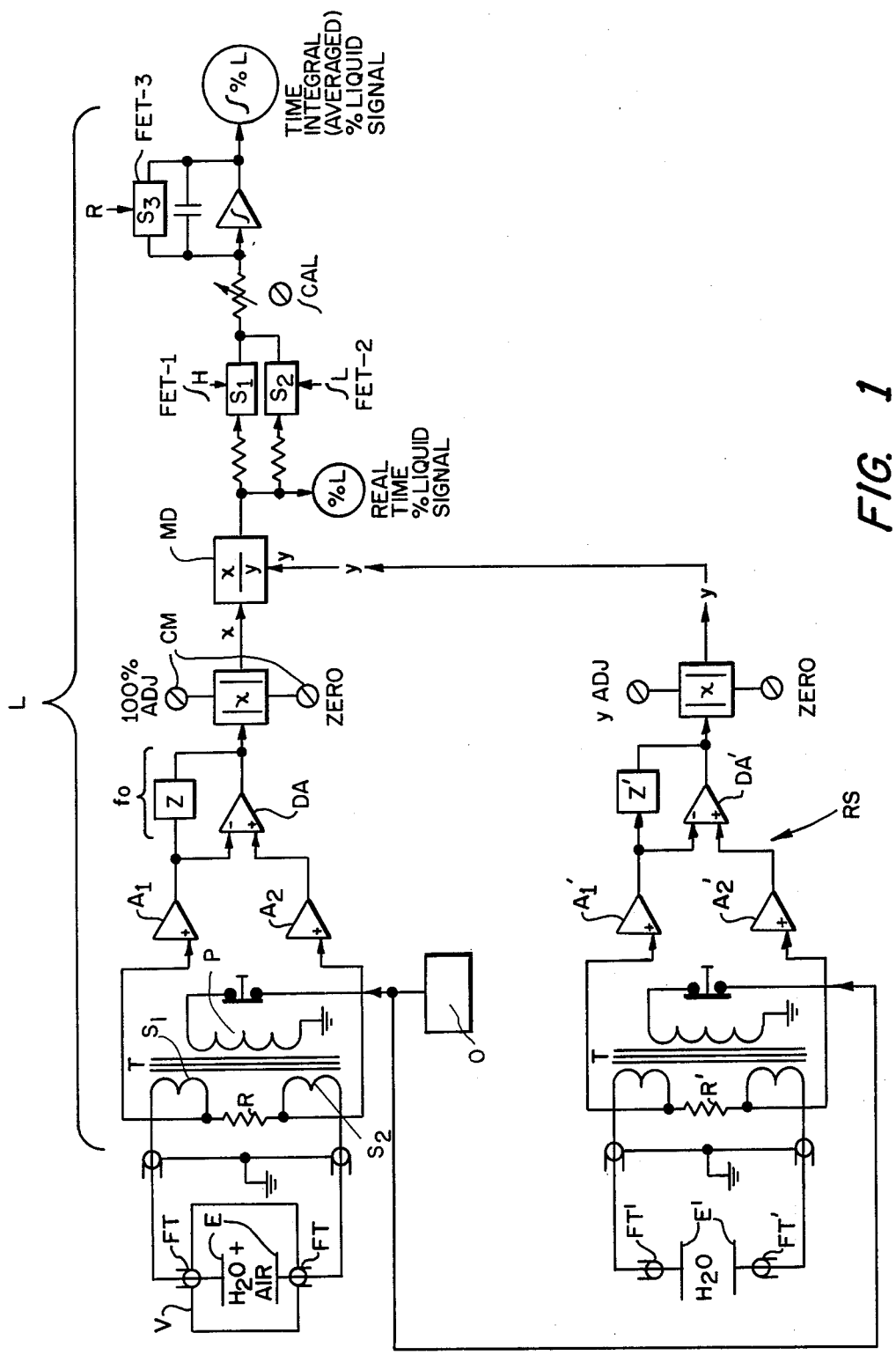
FIG. 1 is a block diagram of the measuring system serving a single station pair of poled electrodes in a mixed phase fluid in accordance with a preferred embodiment of the invention and FIG. 2 is a block diagram of an averaging control for FIG. 3 is a schematic circuit diagram of the FIGS. 1-2 apparatus and FIG. 4 shows the averaging control portion of the FIG. 3 circuit.
Figure 2:
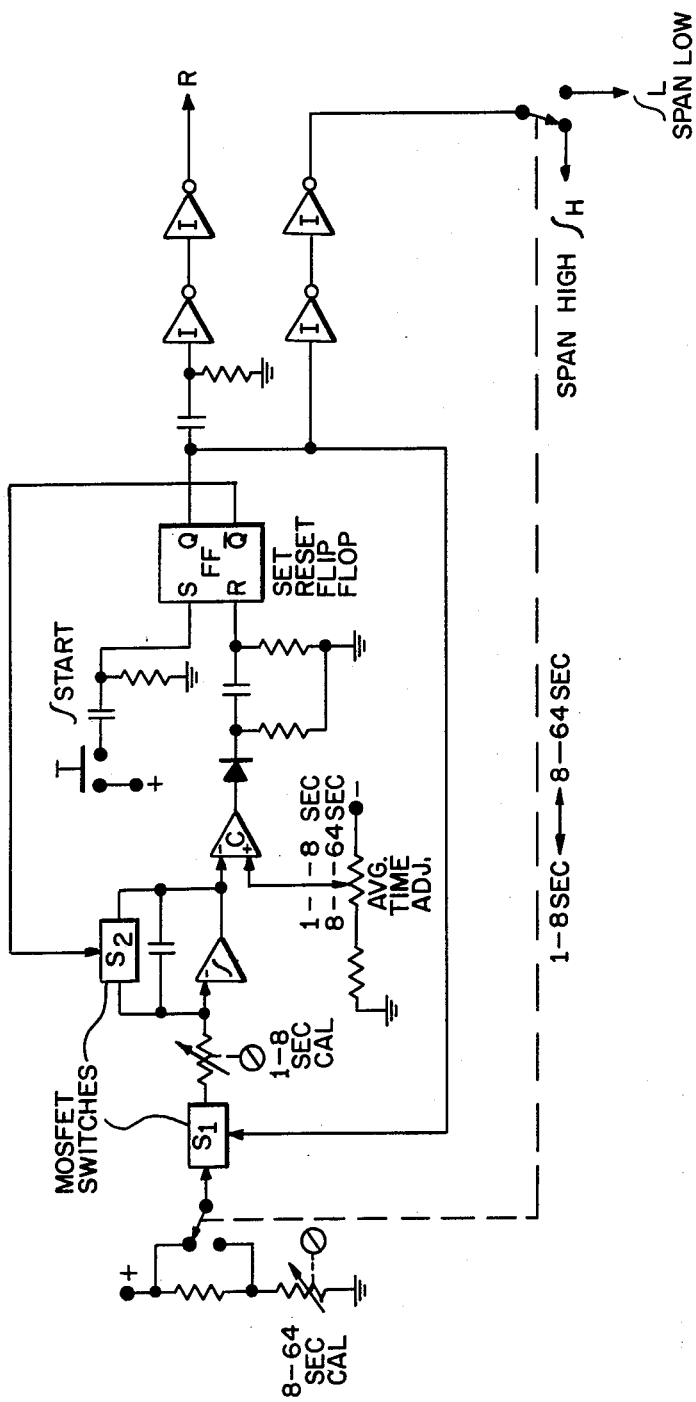
Figure 4:
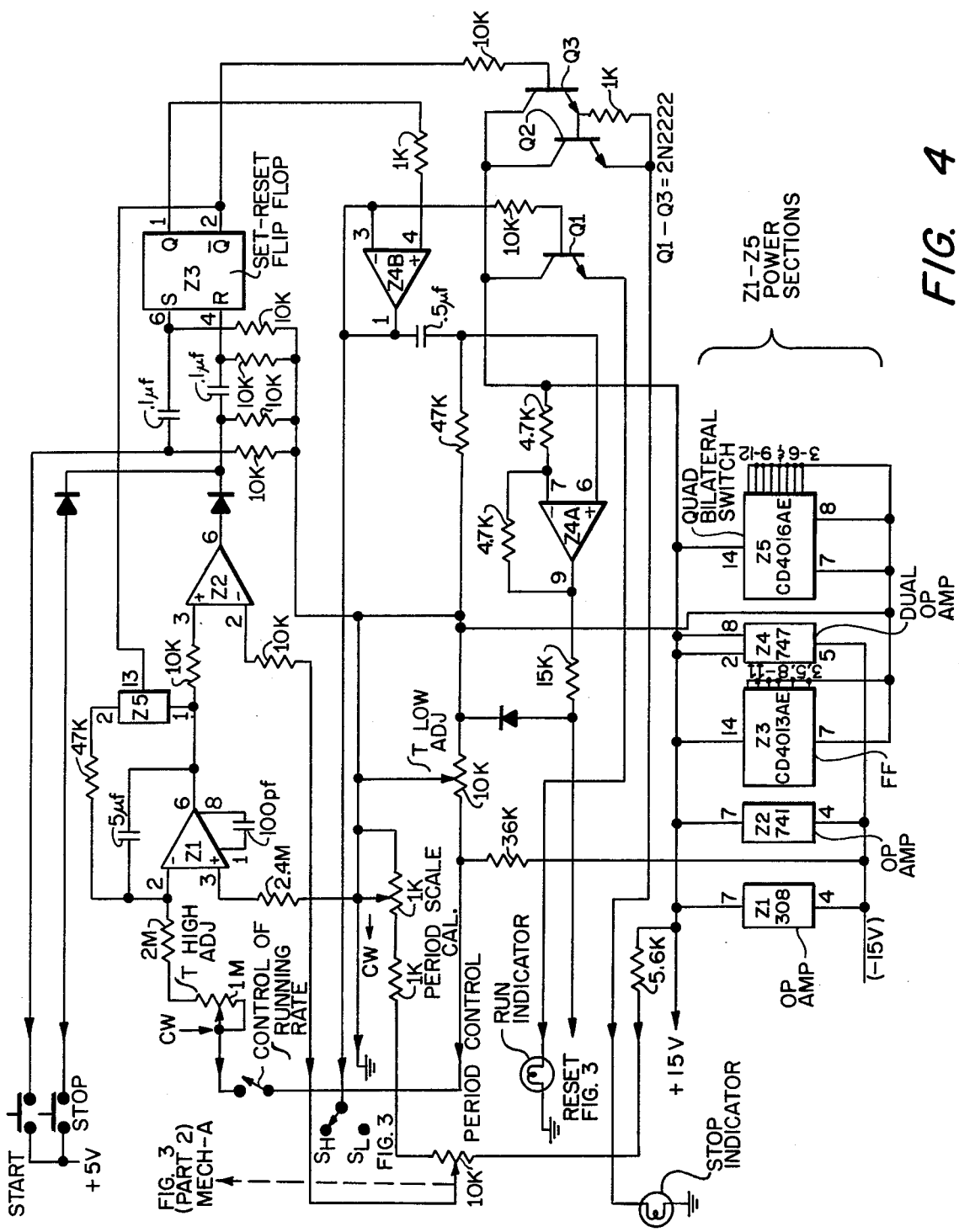

Referring now to FIGS. 1-4, it is shown that the sensor of the invention comprises a fluid containing vessel indicated schematically at V and containing therein electrodes E which are wired via insulating feed throughs to a measuring loop circuit L.

A 5 kilohertz oscillator indicated at O provides driving voltage to the circuits via a transformer T. Sections S1 and S2 show the secondary windings of a transformer with a primary winding P being connected to the oscillator voltage source, the secondary windings being in a series with a low impedance (preferably 5–15 ohms) resistor R, i.e., at least two orders of magnitude (powers of 10) less than impedance between electrodes E.

Taps are taken on both sides of the load resistor through non-inverting amplifiers $A_1$ and $A_2$ whose outputs are connected to a differential amplifier indicated at DA and whose output is taken through a high pass filter $f_o$ to an absolute value (rectified) circuit | X | with calibration means CM which produces an output X which can be divided by a reference signal Y using a multiplier/divider MD (e.g., Intronics 530J four quadrant multiplier/divider or equivalent). The reference signal Y is produced by a reference control circuit RS which is similar to the main circuit and is tied to electrodes E' in a 100% liquid derived from or so related to the fluid measured at electrodes E to have the same intrinsic conductivity and fed to an absolute value circuit REF with calibration means Z and S to provide a quotient which can be fed to a meter M to indicate percent liquid in the sensor. The quotient is established by a reference sensor located in the liquid only and which is also excited by the oscillator O. As stated above, this compensates for changes in bulk conductivity of the fluid medium in vessel V.

The isolation transformers T in each circuit is of low output impedance, on the order of 5 to 15 ohms and the load resistor of each loop has a load value on the order of 5 ohms so that changes in conductivity between electrodes will primarily control the current through the loop and hence the voltage across the load resistor will represent the true conductivity between the electrodes. The isolation transformer also prevents spurious current paths through other electrodes, other sensors and power ground loops.

The non-inverting inputs of the two operational amplifiers $A_1$ and $A_2$ are employed to provide high impedance connections (on the order of 5 to 20 megohms) to the load resistor minimizing the possibility of extraneous current paths. The outputs of the operational amplifiers $A_1$ and $A_2$ are combined by differential amplifier DA to form a signal referenced to ground.

The operating frequency in each phase established by the three phase oscillator is about 5 kilohertz, but may be as low as 1 kilohertz or as high as 30 kilohertz. This is greatly displaced from the competing frequency operations of power equipment and radio equipment.

The operational amplifiers employed throughout the circuitry are bipolar differential input devices with high input and low output impedances; also they are of IC (integrated circuit) construction and are selected such that their high frequency cut-off is higher than the operating frequency.

The fluid may be monitored by the operator in real time (%L) or if desired, the operator may initiate an averaging cycle such that the measuring is averaged over a period which may be set from 1 to 100 or more seconds. The average value may be stored, permitting the operator to read out the average liquid fraction at his convenience.

Although liquid (or void) fraction measurements have been made in water streams using the total impedance method, they have generally been singular or non-multiple measurements. In accordance with the invention, multiple measurements at up to several dozen stations can be made in a common conductive medium (water) and therefore great care must be taken to insure that no cross conduction either resistive or reactive can occur between channels as this would render the system useless.

Several forms of isolation are provided:

Transformer isolation from a common approximately 5 khz sine wave oscillator/driver circuit.

By splitting the secondary of the transformer and placing load resistor R between reactive potentials are balanced to ground.

Shielding of the leads to the electrodes is employed to prevent capacitive cross talk between electrode leads.

A unique arrangement of three operational amplifiers is employed to provide both a differential input for the rejection of common mode signals and an extremely high input impedance to provide no path for current flow through the system power supply.

The total of the secondary impedances and the value of the load resistor will be less than 1/100 of lowest anticipated water resistance between the electrodes, (experimentation has shown that resistivity will greatly predominate over reactance.)

Since the voltage drop across the load resistor is a direct function the current through the resistor, the voltage is directly proportional to the admittance between the electrodes which is essentially proportional to the liquid fraction between the electrodes.

The voltage across the load resistance is presented to the non-inverting inputs of two operational amplifiers. In this mode of operation, the amplifiers exhibit a very high input resistance, thus effectively isolating the electrodes.

A next operational amplifier stage serves two purposes; first it provides a differential input for the outputs of the previous amplifiers to produce a signal in reference to system ground. Second, a narrow band rejection filter is used in the feed-ack path to peak the frequency response at the operating frequency (preferably about 5 khz).

The signal is next passed to an absolute value circuit (perfect rectification). The circuit is an arrangement of two operational amplifiers and as such will also include gain adjustment (100% Adj.) and zero adjustment.

At this point, a voltage signal is available that is proportional to the admittance between the electrodes E. Normally, if the resistivity of the water passing through the system is changing, the apparent liquid fraction would also change resulting in errors. However, since the reference channel is exposed to the same water with no void, the resultant output of the reference channel is a signal proportional to the basic water admittance.

The admittance affected electrical signal is passed to an analog divider where it is divided by the reference (Y) signal. If the resistivity of the water should increase, the admittance signals would both drop, however, this quotient will remain constant thus compensating for the resistivity change.

At this point, a voltage signal proportional to liquid fraction is available, permitting one to effectively monitor the proportion of liquid to vapor fraction, crosstalk and resistivity changes notwithstanding.

AVERAGING CONTROL

The averaging range of 1-64 seconds is broken into two ranges of 1-8 and 8-64 seconds to provide reasonable dynamic range requirements for the circuitry.

The equation for averaging in terms of time is:

$$A = \frac{1}{T} \int_x^T dt$$

Since T is treated as a constant it may be applied before or after integration, hence a fixed integration rate may be used and correction for the precise time of integration applied later.

When a ∫ start button is depressed the flip-flop FF (FIG. 2) is set, making Q high and causing a pulse to be generated through the two inverter/buffers (I) thus producing a positive pulse at R (reset). Also, a positive level is fed to either ∫ H or ∫ L (dependent on time range). Q being high also activates a bilateral switch ($S_1$) causing the timing integrator (∫) to generate a negative-going ramp of voltage. When the output of the integrator reaches a voltage equal to that of the AVERAGING TIME ADJUSTMENT, the comparator (C) output will go positive resetting the flip-flop (FF) and causing Q to go positive. This also activates $S_2$ and resets the timing integrator to zero and removes the level from either ∫ H or ∫ L.

Two adjustments are provided to allow the timing integrator to be calibrated to precisely 1-8 and 8-64 second ranges.

The ∫ H, ∫ L, and R functions are applied to all channels. The integrator (∫) of each channel is arranged with two bilateral switches ($S_1$ & $S_2$). In the 1-8 second timing range $S_1$ is turned on and in the 8-64 second range, $S_2$ is turned on. The integrator time constants are adjusted so that the output of the integrator will just reach the same voltage as the %L signal when the averaging time is at either the full 8 or 64 second setting and %L is held constant.

A good quality capacitor is used for integration so that it will maintain its charge for several minutes after the averaging period. When another averaging cycle is initiated, the momentary R pulse resets the integrator to zero. The adjustment ∫ CAL is provided to normalize all channels.

The average signals are passed through the variable gain amplifiers which are linked to the averaging time adjustment. For settings less than the full 8 or 64 seconds, the voltage from the channel integrator is amplified by the same factor that the time has been reduced. Hence, if the time is set to 4 seconds, the gain is set at 2 thus providing a true average.

Each position may be selected by a multi position interlocked push-button array. Both the real time and average signals are selected simultaneously. Another two position interlocked push-button array is used to select either %L (L) or average %L (AL) voltages to be presented on the meters.

CALIBRATION PROCEDURE

The monitor is designed to provide a meter reading (real time or averaged) representing zero to 100% available admittance between the electrode paris. Calibration of meter deflection vs. actual void or liquid fraction will have to be determined initially by the user. The term % liquid assumes a linear relationship with the actual liquid fraction; however, some deviation is to be expected and must be determined in situ.

The procedure for aligning the system requires that water with no void fraction be flowing between the electrodes E. If it can be assumed that the water is of average resistivity, the zero and Y adjust of the reference channel are adjusted for ½ scale deflection of the Y meter. Next the individual channels in a multi-channel unit are adjusted by selecting the real time signal (%L) and adjusting for full scale meter deflection.

The averaging timer and individual channel integrator may be checked by using a stop watch, setting the timer control at the two full scale settings (8 and 64 seconds) and checking averaged meter readings of each channel.

There is indicated at CS (FIG. 4) channel selection switching for selectively connecting the meter movement for L or AL, with gain compensation circuitry, to other main channels. The reference channel is also common to such other main channels via a common buss, BUSS.

It is preferred to compensate for variations in homogeneity of void distribution at each measuring station by providing the rotating field vector arrangement shown in said application Ser. No. 719,196.

It is evident that those skilled in the art, once given the benefit of the foregoing disclosure, may now make numerous other uses and modifications of, and departures from the specific embodiments described herein without departing from the inventive concepts. Consequently, the invention is to be construed as embracing each and every novel feature and novel combination of features present in, or possessed by, the apparatus and techniques herein disclosed and limited solely by the scope and spirit of the appended claims.

What is claimed is:

1. Method of determining liquid and vapor fractions in a resistive conductive fluid comprising completing multiple electrical current loops through the fluid by applying a 1-30 kiloherz oscillating voltage to multiple poled electrode pairs immersed in the fluid and measuring the absolute value of an electrical parameter, variable as a function of admittance through each said loop as affected by the admittance of the fluid between electrodes of each such pair, as a measure of the liquid fraction at the time of measurement, while isolating reactive and resistive cross conduction between the said current loops and further isolating external common mode noise and further comprising, generating a similar reference parameter measurement in a bath of 100% liquid fluid related to the fluid to be measured for fraction wherein the fraction parameter measurement is automatically divided by the reference (100% liquid) parameter measurement to establish a quotient related electrical signal.

2. The method of claim 1 as a real time instantaneous measuring method.

3. The method of claim 1 as a protracted time integrated and averaged measuring method.

4. The method of claim 1 wherein said multiple poled pairs of electrodes are used with a common reference and common meter for fraction measurement.

5. Apparatus for practice of the method of claim 1 comprising, means defining said poled pairs of electrodes, means for applying an oscillating voltage thereto, means for completing said current loops including paths through fluid medium between the two electrodes of each pair and further including a load resistance, means for producing a signal of voltage drop across the load resistance as said parameter affected by admittance between the electrodes, the load resistance having terminals connected via separate isolating impedances to a summing circuit.

6. Apparatus in accordance with claim 5 wherein driving voltage is applied via a split secondary transformer with the load resistance and electrode pair connected between split portions of the secondary to balance reactive potentials to ground.

7. Apparatus in accordance with claim 6 wherein the impedance of said load resistor is at least two orders of magnitude (powers of 10) lower than the impedance between the electrodes.

8. Apparatus in accordance with claim 5 wherein said summing circuit is combined with a band pass filter to establish a band pass essentially centered about the oscillator frequency and having a 3dB attenuation at ±0.5 or less of the oscillator frequency.

9. Apparatus in accordance with claim 8 and further comprising means for time integrating liquid fraction coupled with gain compensation.

* * * * *